United States Patent [19]
Hardy, Jr. et al.

[11] 4,269,980
[45] May 26, 1981

[54] (SUBSTITUTED-PHENYL)-1,2,4-TRIAZOLO[4,3-C]PYRIMIDINES AND (SUBSTITUTED-PHENYL)-1,2,4-TRIAZOLO[1,5-C]PYRIMIDINES

[75] Inventors: Robert A. Hardy, Jr., Ridgewood, N.J.; Jannie S. Baker, White Plains; Nicanor Q. Quinones, New York, both of N.Y.

[73] Assignee: American Cyanamid Company, Stamford, Conn.

[21] Appl. No.: 104,526

[22] Filed: Dec. 17, 1979

[51] Int. Cl.³ ........................................... C07D 239/70
[52] U.S. Cl. .................................... 544/256; 424/251

[58] Field of Search ........................ 544/256; 424/251

[56] References Cited
PUBLICATIONS
CA 83 9999(d) 1975.

Primary Examiner—Nicholas S. Rizzo
Attorney, Agent, or Firm—Edward A. Conroy, Jr.

[57] ABSTRACT

This disclosure describes novel 5-, 7-, and 8-(substituted-phenyl)-1,2,4-triazolo[4,3-c]pyrimidines and 5-, 7-, and 8-(substituted-phenyl)-1,2,4-triazolo[1,5-c]pyrimidines and their use as anxiolytic agents.

19 Claims, No Drawings

(SUBSTITUTED-PHENYL)-1,2,4-TRIAZOLO[4,3-C]PYRIMIDINES AND (SUBSTITUTED-PHENYL)-1,2,4-TRIAZOLO[1,5-C]PYRIMIDINES

BRIEF SUMMARY OF THE INVENTION

This invention relates to new organic compounds and, more particularly, is concerned with novel 5-, 7-, and 8-(substituted-phenyl)-1,2,4-triazolo[4,3-c]pyrimidines and 5-, 7-, and 8-(substituted-phenyl)-1,2,4-triazolo[1,5-c]-pyrimidines which may be represented by the following structural formula:

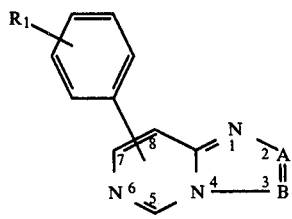

wherein —A=B— is

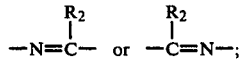

$R_1$ is selected from the group consisting of hydrogen, chloro, fluoro, trifluoromethyl and lower alkoxy ($C_1$–$C_3$); and $R_2$ is selected from the group consisting of hydrogen and lower alkyl ($C_1$–$C_3$). The invention also includes novel compositions of matter containing the above defined compounds which are useful as anxiolytic agents and the method of meliorating anxiety in mammals therewith.

DETAILED DESCRIPTION OF THE INVENTION

The novel compounds of the present invention are, in general, colorless or yellow crystalline solids which are generally soluble in organic solvents such as chloroform, dichloromethane, tetrahydrofuran, acetone, N,N-dimethylformamide, acetic acid and lower alkanols.

Preparation of the novel (substituted-phenyl)-1,2,4-triazolo[4,3-c]pyrimidines (C) of this invention which exhibit anxiolytic activity is carried out according to Scheme I by reacting a 4-hydrazino (substituted-phenyl)pyrimidine of formula (A) with lower alkyl orthoformates, lower alkyl orthoacetates or lower alkyl orthopropionates (B) to give the desired compounds (C) wherein $R_1$ and $R_2$ are as previously defined.

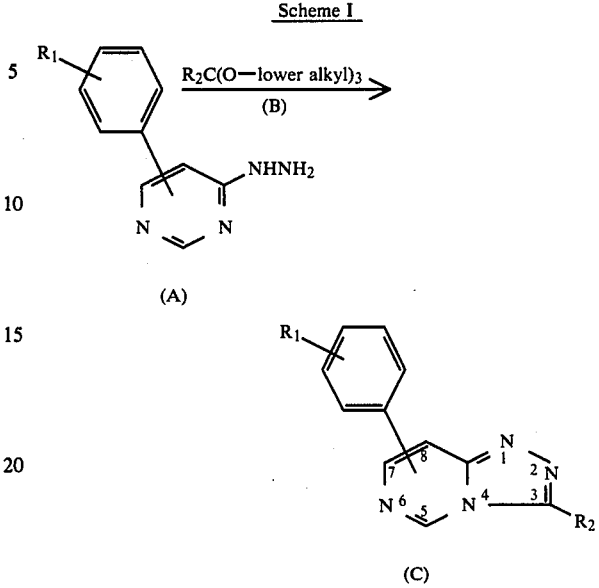

An alternate reagent for the above cyclization is diethoxymethylacetate [$CH_3COOCH(OC_2H_5)_2$]; in this case the cyclization product (C) has $R_2$=H. The rate and relative ease of the above cyclization varies widely with the composition of the hydrazine intermediate (A); i.e. the position of the substituted phenyl group (5-, 7- or 8-) and the nature of the phenyl substituent. For example, cyclization of 5-aryl-4-hydrazinopyrimidines to give 8-aryl-1,2,4-triazolo[4,3-c]pyrimidines is particularly rapid. Treatment with ortho esters at room temperature, or at 75°–80° C. for a short time, effects cyclization to (C); and cyclization with diethoxymethyl acetate is usually complete within a few minutes at room temperature. In contrast, cyclization of 6-aryl-4-hydrazinopyrimidines to give 7-aryl-1,2,4-triazolo[4,3-c]pyrimidines requires more conventional time and temperature conditions; heating in an excess of the ortho ester for several hours or longer. The hydrazine is generally treated with an excess of the cyclizing reagent (ortho ester or diethoxymethyl acetate) without any additional solvent. The temperature range is from about 20° to about 150° C., and the time may range from a few minutes a room temperature to refluxing for several hours, or 24–72 hours at room temperature. The varying conditions for the above cyclization of differently substituted hydrazines (A) are further illustrated in the appended examples.

Extended treatment of the hydrazines (A), described above, with the above cyclization reagents may also produce (substituted-phenyl)-1,2,4-triazolo[1,5-c]pyrimidines of formula (D) which are also included in the present invention. This is effected by the isomerization reaction outlined in Scheme II, and represents a convenient and practical synthesis of the [1,5-c]isomers (D):

Scheme II

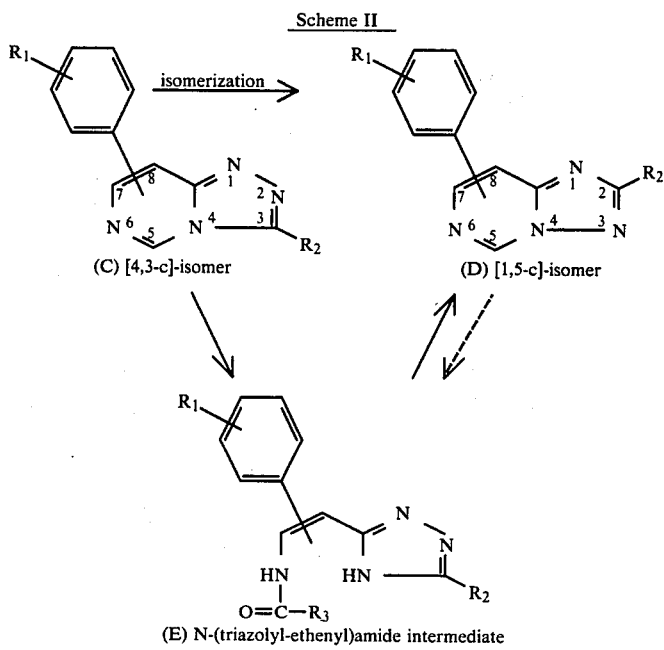

(E) N-(triazolyl-ethenyl)amide intermediate wherein $R_1$ and $R_2$ are as previously defined and $R_3$ is H when

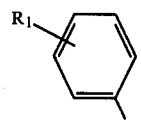

in (C) and (D) is attached in the 7 or 8 position; and $R_3$ is

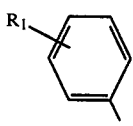

when this group in (C) and (D) is attached in the 5-position.

This rearrangement may be considered a Dimroth-like rearrangement [D. J. Brown and T. Nagamatsu, Australian J. Chem., 30, 2515 (1977); and 31, 2505 (1978) and references therein] in which a variety of conditions are known to effect the transformation, including extended treatment with ortho esters as described above (references cited above). These also include rearrangement under acidic and basic conditions. Refluxing formic or acetic acids are commonly used. The triazolyl-ethenyl-amide (E) may be considered as intermediate in the rearrangement where this transformation is carried out in hydroxylic solvents or solvents containing traces of water. In some cases it may be isolated as a discrete compound, purified and characterized as such. In other cases, it may be formed in situ and recyclized to the thermodynamically more stable [1,5-c]-isomer(D) without isolation. The amides (E) are also obtained by heating the triazolyl-pyrimidines (C) and (D) in aqueous media, and recyclization of (E) to isomer-(D) may be effected either by fusion or by heating in acidic media such as acetic and formic acids. Rearrangement of (C) to (D), in selected cases, may also be carried out thermally by heating the [4,3-c]-isomer (C) above its melting point for a short time. The [1,5-c]-isomer (D) is thereby produced; this thermal isomerization is not considered to take place via the intermediate amide (E).

As with the widespread variation in the rate of the hydrazine cyclization described above (Scheme I), the ease of Dimroth-like rearrangement (Scheme II) also varies markedly with position and nature of the phenyl substituent. For example, 8-aryl-1,2,4-triazolo[4,3-c]pyrimidines rearrange to 8-aryl-1,2,4-triazolo[1,5-c]pyrimidines with particular ease: unexpectedly, methanol at room temperature or at the reflux temperature has been found to effect complete rearrangement with these compounds. In contrast, 5-aryl-1,2,4-triazolo[4,3-c]pyrimidines are recovered unchanged after refluxing in methanol for several days. Overall, cyclization of the pyrimidyl-hydrazine intermediates (A) and rearrangement of the initial cyclization products, the [4,3-c]-compounds (C), to the [1,5-c]-isomers (D) is governed by the severity of the conditions used, longer heating and higher temperatures generally producing greater conversion to the [1,5-c]-isomers. The varying conditions for cyclization of differently substituted 4-hydrazinopyrimidines and rearrangement of a variety of different [4,3-c]-isomers are further illustrated in the appended examples.

The isomeric new products of this invention are readily distinguished by their spectral and physical properties. For example, the [4,3-c]-compounds are generally higher melting and less soluble than their comparable [1,5-c]-isomers. Thin-layer chromatography (TLC) in most cases, readily distinguishes between isomers and mixtures of isomers, the higher-melting, less soluble isomer being distinctly more polar. Selective crystallization from a suitable solvent generally gives the desired product, (C) or (D), in substantially pure form. Chromatographic methods of purification well known to those skilled in the art may also be employed.

Both proton magnetic resonance spectra (PMR), and ultraviolet spectra (UV) have proven characteristic for the [4,3-c]-derivatives (C) and [1,5-c]-isomers (D) of this invention. The proton or methyl substituents on the triazolo ring show characteristic chemical shifts (PMR) in each series when the corresponding isomers are compared: ca 9.3–9.5 for H-3 in the 7- and 8-aryl-[4,3-c]-isomers, ca 9.05 for H-3 in the 5-aryl-[4,3-c]-isomers, and ca 2.8–2.9 for 3-$CH_3$ in the 7- and 8-aryl-[4,3-c]-series; contrasting with ca 8.4–8.5 for H-3 in the 8-aryl-[1,5-c]-isomers and ca 2.6–2.7 for 3-$CH_3$ in the 7-and 8-aryl[1,5-c]-isomers. The two pyrimidine proton signals are also characteristic for the [4,3-c]- and [1,5-c]-isomers.

An alternate method for preparing the [4,3-c]- and [1,5-c]-isomers of this invention is illustrated as follows:

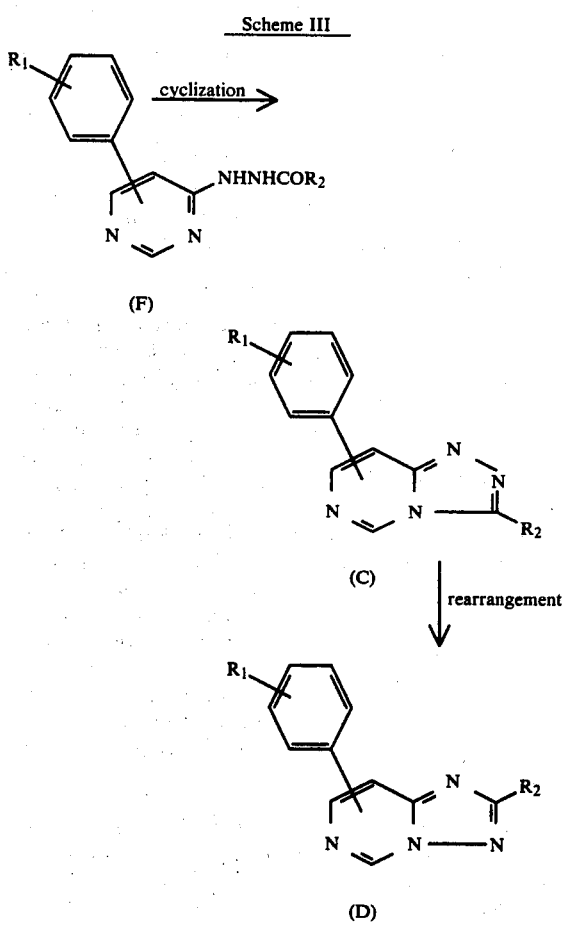

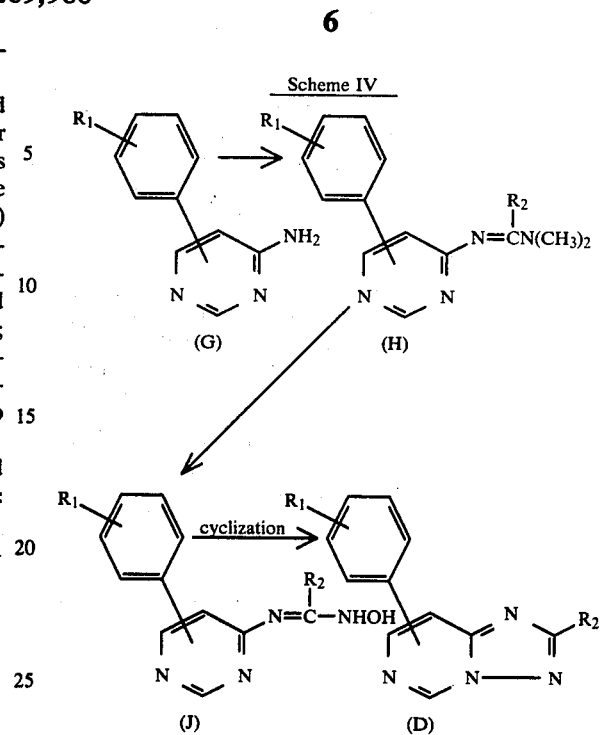

wherein $R_1$ and $R_2$ are as previously defined. By this method, an acylhydrazino-pyrimidine (F) is cyclized using known methods, and the resulting triazolo-[4,3-c]pyrimidine (C) is either isolated as such or rearranged directly to the triazolo[1,5-c]pyrimidine (D) using the methods described above. Cyclization methods include phosphorus oxychloride, heating, and, in some cases, heating with formic or acetic acids.

Another method for preparation of the 1,2,4-triazolo[1,5-c]pyrimidines of this invention is also illustrated as follows:

wherein $R_1$ and $R_2$ are as previously described. By this scheme a suitably substituted-phenyl 4-aminopyrimidine (G) is converted to the dimethylaminoethylene derivative (H), for example with dimethylformamide dimethylacetal ($R_2$=H), which is in turn transformed to the hydroxylamino intermediate (J); this intermediate (J) is cyclized under acidic conditions, for example with polyphosphoric acid.

The 2-, 5- and 6-aryl-4-hydrazinopyrimidine intermediates (A) [and the 4-amino-derivatives (G)] are readily prepared by well known methods. For example, the substituted-phenyl 4-hydroxyprimidines (which are also known, as their tautomers, the corresponding pyrimidinones) are converted to the 4-chloropyrimidines by treatment with phosphorus oxychloride, followed by treatment of the chloro derivative with hydrazine to give the desired hydrazino-pyrimidine (A). Preparation of 2-aryl-4-hydrazinopyrimidines and 4-aryl-6-hydrazinopyrimidines by these methods has been described by Vanderhaeghe and Claesen, Bull. Soc. Chime. Belg., 68, 30 (1959) [Chem. Abstr., 56, 10144i (1962)]. The analogous preparation of 5-aryl-4-hydrazinopyrimidines has been described by Tsatsaronis and co-workers, Rec. Trav. Chim. Pays-Bas, 90, 584 (1961) [Chem. Abstr., 75, 76725j (1971)], and Chem. Ber., 94, 2876 (1961) [Chem. Abstr., 56, 7320c (1962)].

The novel compounds of the present invention posses central nervous system activity at non-toxic doses and as such as useful as anxiolytic agents. That is, they produce certain responses in standard tests with laboratory animals which are known to correlate well with relief of anxiety in man. The compounds have been tested pharmacologically and found to have such properties with a desirable wide spread between doses producing anxiolytic activity and toxic symptoms.

The anti-anxiety properties of the novel compounds of the present invention are established in a test which indicates anxiolytic activity by the measure of protection from convulsions resulting from the administration of pentylenetetrazole. Single or graded dose levels of the test compounds are administered orally or intraperitoneally in a 2% starch vehicle, containing 0.5% v/v polyethylene glycol and one drop of polysorbate 80 to groups of at least 4 rats. At 30 or 60 minutes, the rats are treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Aminal testing and Screening Procedures in Evaluating Psychotropic Drugs" in "An Introduction to Psychopharmacology", Eds. R. R. Rech and K. E. Moore, Raven Press, New York pp. 237–288 (1971)] that there is a high degree of correlation between antagonism of pentylenetetrazole seizures in rats and anti-anxiety effects in higher warm-blooded animals. The following representative compounds of the present invention listed in Table I have been shown to possess anxiolytic activity when tested as described above.

TABLE I

Protection Against Clonic Seizures Caused By pentylenetetrazole In Rats

| Compound | Result* |
|---|---|
| 8-(4-Chlorophenyl)-3-methyl-1,2,4-triazolo[4,3-c]pyrimidine | Active |
| 8-[3-(Trifluoromethyl)phenyl]-1,2,4-triazolo[4,3-c]pyrimidine | Active |
| 2-Methyl-8-[3-(trifluoromethyl)phenyl]-1,2,4-triazolo[1,5-c]pyrimidine | Active |
| 3-Methyl-8-[3-(trifluoromethyl)phenyl]-1,2,4-triazolo[4,3-c]pyrimidine | Active |
| 2-Methyl-7-phenyl-1,2,4-triazolo-[1,5-c]pyrimidine | Active |
| 5-Phenyl-1,2,4-triazolo[4,3-c]pyrimidine | Active |
| 8-(3-Fluorophenyl)-1,2,4-triazolo[4,3-c]pyrimidine | Active |
| 5-[3-(Trifluoromethyl)phenyl]-1,2,4-triazolo[4,3-c]pyrimidine | Active |
| 8-(3-Fluorophenyl)-2-methyl-1,2,4-triazolo[1,5-c]pyrimidine | Active |
| 8-(2-Chlorophenyl)-1,2,4-triazolo-[1,5-c]pyrimidine | Active |
| 8-(2-Chlorophenyl)-2-methyl-1,2,4-triazolo[1,5-c]pyrimidine | Active |
| 8-(2-Chlorophenyl)-3-methyl-1,2,4-triazolo[4,3-c]pyrimidine | Active |
| 8-(2-Chlorophenyl)-1,2,4-triazolo-[4,3-c]pyrimidine | Active |
| 5-[3-Methoxyphenyl)-1,2,4-triazolo-[4,3-c]pyrimidine | Active |
| 5-(3-Chlorophenyl)-1,2,4-triazolo-[4,3-c]pyrimidine | Active |
| 7-[3-(Trifluoromethyl)-phenyl]-1,2,4-triazolo[1,5-c]pyrimidine | Active |
| 5-(2-Fluorophenyl)-1,2,4-triazolo-[4,3-c]pyrimidine | Active |

*Test compounds are administered intrapertioneally at a dose of 50 mg./kg., 30 minutes before treatment with pentylenetetrazole.

Known antipsychotics such as chlorpromazine and haloperidol protect grouped mice from the lethal effects of d-amphetamine sulfate. Other types of "tranquilizers" such as Librium and Valium are ineffective. The following method is a modification of the method of Lasagna, L. and McCann, W. P., A test for tranquilizing drugs, Arch. Int. Pharmacodyn., 113, 290–295 (1958).

Groups of 10 mice are treated with the compound at an intraperitoneal dose of 20 mg./kg. and placed in wire mesh cages. After thirty minutes, the mice are given intraperitoneal injections of d-amphetamine sulfate (in saline) at a dose of 15 mg./kg. which is estimated to cause 90 to 100% deaths in grouped mice. Deaths are recorded 18 to 24 hours later. Vehicle and chlorpromazine (5 mg./kg.) are utilized as placebo and positive controls, respectively, with each test group. The time of peak effect is established as the absorption time for the respective compounds that protect the greatest percentage of mice from death within 24 hours, with equal to or greater than 60% protection being considered active.

TABLE II

| Neuroleptic Screening Grouped Amphetamine Lethality | |
|---|---|
| Compound | Result |
| 3-Methyl-7-phenyl-1,2,4-triazolo[4,3-c]pyrimidine | Active |

The novel compounds of the present invention have been found to be highly useful for meliorating anxiety in mammals when administered in amounts ranging from about 0.5 mg. to about 50.0 mg./kg. of body weight per day. A preferred dosage regimen for optimum results would be from about 1.0 mg. to about 10.0 mg./kg. of body weight per day. Such dosage units are employed that contain a total of from about 10 to about 200 mg. of active compound. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl- and propylparabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl- and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

8-(4-Chlorophenyl)-1,2,4-triazolo[4,3-c]pyrimidine

A mixture of 2.0 g. of 5-(4-chlorophenyl)-4-hydrazinopyrimidine is shaken with 10 ml. of diethoxymethyl acetate. The mixture is allowed to stand 15–30 minutes and then is diluted with hexane. The precipitated product (1.81 g: 83%) is collected and recrystallized from ethanol to give the title compound; m.p. 193°–195° C.

EXAMPLE 2

3-Methyl-8-[3-(trifluoromethyl)phenyl]-1,2,4-triazolo[4,3-c]pyrimidine

A mixture of 1.0 g. of 4-hydrazino-5-(3-trifluoromethylphenyl)pyrimidine and 10–12 ml. of triethyl orthoacetate is stirred at room temperature. Complete solution is effected in about 10 minutes and stirring is continued for an additional 30–40 minutes until a new precipitate begins to form. This precipitate is collected in 3 crops over a 4 hour period to yield 0.85 g. (77%) of product. The product is recrystallized from chloroform-hexane to give the title compound, m.p. 157°–159° C.

When this reaction is carried out at the reflux temperature for 1–2 hours, the yield of the above product is lower (30%) due to gradual isomerization to 2-methyl-8-[3-(trifluoromethyl)phenyl][1,5-c]pyrimidine (see Example 14).

EXAMPLES 3 TO 12

Procedures similar to those described in Examples 1 and 2 are employed to prepare the 8-aryl-1,2,4-triazolo[4,3-c]pyrimidine compounds listed in Table III.

TABLE III

8-Aryl-1,2,4-triazolo[4,3-c]pyrimidines

| Example | Compound | Procedure Used | $R_1$ | $R_2$ | M.P. °C. | Crystallization Solvent |
|---|---|---|---|---|---|---|
| 3 | 8-(4-Chlorophenyl)-3-methyl-1,2,4-triazolo[4,3-c]-pyrimidine | triethyl orthoacetate 75–80° C. 2–3 hours | 4-Cl | $CH_3$ | 188–189 | triethyl orthoacetate |
| 4 | 8-[3-(Trifluoromethyl)phenyl]-1,2,4-triazolo[4,3-c]-pyrimidine | diethoxymethyl acetate room temperature 20 hours | 3-$CF_3$ | H | 183–185 | ethyl acetate/ hexane |
| 5 | 8-(3-Fluorophenyl)-1,2,4-triazolo[4,3-c]pyrimidine | diethoxymethyl acetate room temperature 45 minutes | 3-F | H | 185–186 | diethoxymethyl acetate |
| 6 | 8-(3-Chlorophenyl)-1,2,4-triazolo[4,3-c]pyrimidine | diethoxymethyl acetate room temperature 45 minutes | 3-Cl | H | 188–190 | diethoxymethyl acetate |
| 7 | 8-(3-Chlorophenyl)-3-methyl- | triethyl | 3-Cl | $CH_3$ | 168–169 | ethyl acetate |

TABLE III-continued

8-Aryl-1,2,4-triazolo[4,3-c]pyrimidines

| Example | Compound | Procedure Used | $R_1$ | $R_2$ | M.P. °C. | Crystallization Solvent |
|---|---|---|---|---|---|---|
| | 1,2,4-triazolo[4,3-c]-pyrimdine | orthoacetate 75° C. one hour | | | | |
| 8 | 8-(3-Fluorophenyl)-3-methyl-1,2,4-triazolo[4,3-c]-pyrimidine | triethyl orthoacetate 75° C. 1–2 hours | 3-F | $CH_3$ | 171–173 | ethyl acetate |
| 9 | 8-(4-Methoxyphenyl)-1,2,4-triazolo[4,3-c]pyrimidine | diethoxymethyl acetate room temperature 15–30 minutes | 4-$CH_3O$ | H | 167–169 | ethyl acetate |
| 10 | 8-(2-Chlorophenyl)-3-methyl-1,2,4-triazolo[4,3-c]-pyrimidine | triethyl orthoacetate 75–80° C. 2 hours | 2-Cl | $CH_3$ | 135–136 | methylene chloride/hexane |
| 11 | 8-(2-Chlorophenyl)-1,2,4-triazolo[4,3-c]pyrimidine | diethoxymethyl acetate room temperature 15–30 minutes | 2-Cl | H | 219–220 | methylene chloride/hexane |
| 12 | 3-Methyl-8-phenyl 1,2,4-triazolo-[4,3-c]pyrimidine | triethyl orthoacetate reflux temperature 5 hours | H | $CH_3$ | 159–160 | hexane |

EXAMPLE 13

8-(4-Chlorophenyl)-1,2,4-triazolo[1,5-c]pyrimidine

A mixture of 1.76 g. of 8-(4-chlorophenyl)-1,2,4-triazolo[4,3-c]pyrimidine and 25 ml. of methanol is heated at the reflux temperature for 18 hours. The reaction mixture is cooled to room temperature to separate a crystalline material which is collected by filtration to give 1.53 g. (83%) of the product of the example, m.p. 154°–155° C.

EXAMPLE 14

2-Methyl-8-[3-(trifluoromethyl)phenyl]-1,2,4-triazolo[1,5-c]pyrimidine

A solution of 0.35 g. of 3-methyl-8-[3-(trifluoromethyl)phenyl]-1,2,4-triazolo[4,3-c]pyrimidine in 5 ml. of methanol is allowed to stand at room temperature. The rearrangement is monitored by thin layer chromatography and is substantially complete after 7 days. The precipitated product is collected by filtration to give 0.14 g. of the product of the example, m.p. 114°–116° C.

EXAMPLES 15 TO 23

Procedures similar to those described in Examples 12 and 13 are employed to prepare the 8-aryl-1,2,4-triazolo[1,5-c]pyrimidine isomers listed in Table IV.

TABLE IV

8-Aryl-1,2,4-triazolo[1,5-c]pyrimidines

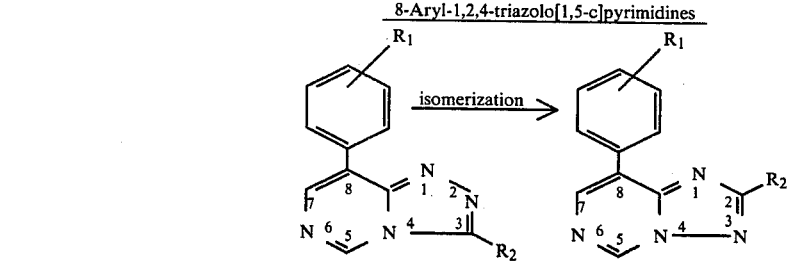

| Example | Compound | Procedure Used | $R_1$ | $R_2$ | M.P. °C. |
|---|---|---|---|---|---|
| 15 | 8-(4-Chlorophenyl)-2-methyl-1,2,4-triazolo[1,5-c]-pyrimidine | methanol reflux 24 hours | 4-Cl | $CH_3$ | 172–173 |
| 16 | 8-[3-(Trifluoromethyl)- | methanol | 3-$CF_3$ | H | 105–106 |

TABLE IV-continued

8-Aryl-1,2,4-triazolo[1,5-c]pyrimidines

| Example | Compound | Procedure Used | $R_1$ | $R_2$ | M.P. °C. |
|---|---|---|---|---|---|
|  | phenyl]-1,2,4-triazolo[1,5-c]pyrimidine | room temperature 4 days |  |  |  |
| 17 | 8-(3-Fluorophenyl)-1,2,4-triazolo[1,5-c]pyrimidine | methanol room temperature 3 days | 3-F | H | 153–154 |
| 18 | 8-(3-Fluorophenyl)-2-methyl-1,2,4-triazolo[1,5-c]pyrimidine | methanol room temperature 18–30 days | 3-F | $CH_3$ | 149–151 |
| 19 | 8-(3-Chlorophenyl)-1,2,4-triazolo[1,5-c]pyrimidine | methanol reflux 18 hours | 3-Cl | H | 160–161 |
| 20 | 8-(3-Chlorophenyl)-2-methyl-1,2,4-triazolo[1,5-c]pyrimidine | methanol reflux 30 hours | 3-Cl | $CH_3$ | 147–149 |
| 21 | 8-(4-Methoxyphenyl)-1,2,4-triazolo[1,5-c]pyrimidine | methanol reflux 18 hours | 4-$CH_3O$ | H | 137–139 |
| 22 | 8-(2-Chlorophenyl)-1,2,4-triazolo[1,5-c]pyrimidine | methanol reflux 18 hours | 2-Cl | H | 132–133 |
| 23 | 8-(2-Chlorophenyl)-2-methyl-1,2,4-triazolo[1,5-c]pyrimidine | methanol reflux 24 hours | 2-Cl | $CH_3$ | 144–145 |

EXAMPLE 24

5-[3-(Trifluoromethyl)phenyl]-1,2,4-triazolo[4,3-c]pyrimidine

The general procedure of Example 1 is repeated: A solution of 0.300 g. of 4-hydrazino-2-[3-(trifluoromethyl)phenyl]pyrimidine and 1 ml. of diethoxymethyl acetate is stirred at room temperature for 24 hours. The mixture is diluted with an excess of petroleum ether and the precipitate which forms is collected after 20–30 minutes to give 0.182 g. of the product of the example; m.p. 145°–146° C. when recrystallized from chloroform/hexane.

EXAMPLES 25 TO 30

By the procedure described in Example 24 the compounds of Table V are prepared.

TABLE V

5-Aryl-1,2,4-triazolo[4,3-c]pyrimidines

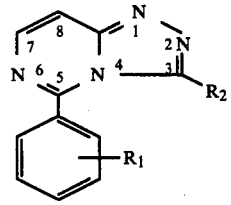

| Example | Compound | Procedure Used | $R_1$ | $R_2$ | M.P. °C. | Crystallization Solvent |
|---|---|---|---|---|---|---|
| 25 | 5-Phenyl-1,2,4-triazolo[4,3-c]pyrimidine | diethoxymethyl acetate room temperature 3 days | H | H | 158–160 | chloroform/hexane |
| 26 | 5-(4-Chlorophenyl)-1,2,4-triazolo[4,3-c]pyrimidine | diethoxymethyl acetate room temperature 20–24 hours | 4-Cl | H | 245 | chloroform/hexane |
| 27 | 5-(3-Chlorophenyl)-1,2,4-triazolo[4,3-c]pyrimidine | dimethoxymethyl acetate room temperature 20 hours | 3-Cl | H | 180–183 | petroleum ether |
| 28 | 5-(2-Fluorophenyl)-1,2,4-triazolo[4,3-c]pyrimidine | dimethoxymethyl acetate room temperature 16 hours | 2-F | H | 120–122 | methylene chloride/hexane |

TABLE V-continued

5-Aryl-1,2,4-triazolo[4,3-c]pyrimidines

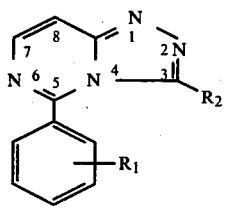

| Example | Compound | Procedure Used | $R_1$ | $R_2$ | M.P. °C. | Crystallization Solvent |
|---|---|---|---|---|---|---|
| 29 | 5-(3-Methoxyphenyl)-1,2,4-triazolo[4,3-c]pyrimidine | dimethoxymethyl acetate room temperature 20 hours | 3-CH$_3$O | H | 183–185 | methylene chloride/hexane |
| 30 | 5-(4-Fluorophenyl)-1,2,4-triazolo[4,3-c]pyrimidine | dimethoxymethyl acetate room temperature 24 hours | 4-F | H | 166–169 | methylene chloride/hexane |

EXAMPLE 31

2-Methyl-5-phenyl-1,2,4-triazolo[1,5-c]-pyrimidine

A mixture of 0.27 g. of 1-acetyl-2-(2-phenyl-pyrimidin-4-yl)hydrazine is stirred with 3 ml. of phosphorus oxychloride at about 100° C. for 7½ hours. The mixture is diluted with chloroform (25 ml.) and evaporated under reduced pressure to remove excess phosphorus oxychloride. The addition of chloroform and evaporation is repeated, and the residue is taken up in chloroform. The chloroform solution is washed with water, with 5% sodium bicarbonate solution, then with water again, dried over anhydrous sulfate and evaporated to give the crude product. This is purified by fractional crystallization from hexane, triturating the solid with boiling hexane, filtering and evaporating the filtrate to a small volume. The product of the example, m.p. 68°–71° C., is thereby obtained.

EXAMPLE 32

2-Methyl-5-[3-(trifluoromethyl)-phenyl]1,2,4-triazolo[1,5-c]-pyrimidine

The procedure of Example 31 is repeated. 1-Acetyl-2-[2-(3-trifluoromethyl-phenyl)-pyrimidin-4-yl]hydrazine is heated with phosphorus oxychloride and the product of the example is isolated from the reaction mixture.

EXAMPLE 33

α,α,α-Trifluoro-N-[2-(5-methyl-1,2,4-triazol-3-yl)ethenyl]-m-toluamide

A mixture of 1-acetyl-2-[2-(3-trifluoromethylphenyl)-pyrimidin-4-yl]hydrazine and 15 ml. of phosphorus oxychloride is heated at the reflux temperature for about 20 hours. The cooled reaction mixture is poured over ice, the aqueous mixture neutralized with saturated sodium bicarbonate solution and the product collected. It is then taken up in ether, the ether dried and then evaporated to a solid residue. This residue is triturated with hexane and the precipitate collected. Recrystallization from chloroform/methanol then gives the product of the example, m.p. 153°–154° C.

EXAMPLE 34

2-Methyl-5-[3-(trifluoromethyl)-phenyl]1,2,4-triazolo[1,5-c]-pyrimidine

The amide from the preceeding example, α,α,α-trifluoro-N-[2-(5-methyl-1,2,4-triazol-3-yl)ethenyl]-m-toluamide, is heated to its fusion point and the product of the example is thereby obtained. This is identical with the product obtained by the procedure described in Example 32.

EXAMPLE 35

N-[2-(5-Methyl-1,2,4-triazol-3-yl)ethenyl]benzamide

A mixture of 1.0 g. of 1-acetyl-2-(2-phenylpyrimidin-4-yl)hydrazine and 10 ml. of phosphorus oxychloride is heated to the reflux temperature, with stirring, for 7 hours. The mixture is cooled to room temperature, melthylene chloride is added and evaporated under reduced pressure to remove excess phosphorus oxychloride. This is repeated, and the residue is taken up in methylene chloride; the organic layer is washed thoroughly with 5% sodium bicarbonate solution, then with water, dried over anhydrous sodium sulfate and evaporated. The residue is a pale yellow solid which is recrystallized from methylene chloride/hexane. The product of the example, m.p. 140°–145°, is thereby obtained.

EXAMPLE 36

2-Methyl-5-phenyl-1,2,4-triazolo[1,5-c]-pyrimidine

The amide from the preceeding example, N-[2-(5-methyl-1,2,4-triazol-3-yl)ethenyl]benzamide, is heated at its fusion point and the title compound is obtained. It is identical with the product obtained by the procedure of Example 31.

EXAMPLE 37

N-[2-(3-Trifluoromethyl-phenyl)-2-(1,2,4-triazol-3-yl)ethenyl]formamide

A mixture of 3.00 g. of 4-hydrazino-5-(3-trifluoromethylphenyl)-pyrimidine and 20 ml. of diethoxymethyl acetate is allowed to stand at room temperature for about 44 hours (similar to Example 2). The reaction mixture is diluted with petroleum ether and the crude product mixture is collected; 2.87 g. (ca 85%), m.p. 138°–143°. This crude product is recrystallized twice from ethyl acetate/hexane to give the product of the example, m.p. 153°–155° C. (approx. 60% yield), as a white powder.

From the filtrate, 0.08 g. of yellowish-white crystals are collected after standing for several days; this is 8-[3-(trifluoromethyl)-phenyl]-1,2,4-triazolo[1,5-c]pyrimidine, identical with the product of Example 16.

Thin layer chromatography of the crude product mixture (2.87 g. above) also indicates the presence of traces of 8-[3-(trifluoromethyl)phenyl]-1,2,4-triazolo[4,3-c]pyrimidine (Example 4).

EXAMPLE 38

8-[3-(trifluoromethyl)-phenyl]-1,2,4-triazolo[1,5-c]pyrimidine

The amide from the preceeding example, N-[2-(3-trifluoromethyl-phenyl)-2-(1,2,4-triazol-3-yl)ethenyl]formamide, is dissolved in methanol and the mixture is heated to the reflux temperature for about 60 hours. The solvent is evaporated and the residue is crystallized with the aid of petroleum ether and collected; the product is thereby obtained and is identical with that obtained in Example 16.

EXAMPLE 39

7-(3-Fluorophenyl)-3-methyl-1,2,4-triazolo[4,3-c]pyrimidine

A mixture of 1.2 g. of 4-(3-fluorophenyl)-6-hydrazinopyrimidine and 12 ml. of triethyl orthoacetate is heated to the reflux temperature. The hydrazinopyrimidine dissolves, and after about one hour a new precipitate begins to form; an additional 5 ml. of triethyl orthoacetate is added and refluxing is continued for a total of 18 hours. The reaction mixture is cooled and filtered to collect the product which is triturated with boiling ethanol. The insoluble precipitate is collected to give the product of the example, m.p. 282°–284° C., free from its more soluble isomer, 7-(3-fluorophenyl)-3-methyl-1,2,4-triazolo[1,5-c]pyrimidine. Alternately, this cyclization may be effected under milder conditions, that is lower temperature and shorter time, in order to minimize the formation of rearranged [1,5-c]isomer.

Cyclization of 4-(3-fluorophenyl)-6-hydrazinopyrimidine with diethoxymethyl acetate at room temperature (as in Example 5) gives 7-(3-fluorophenyl)-1,2,4-triazolo[4,3-c]pyrimidine as the major product together with its isomer, 7-(3-fluorophenyl)-1,2,4-triazolo[1,5-c]pyrimidine as the minor product. The [4,3-c]-isomer may be isolated by suitable methods (i.e. fractional crystallization or chromatography) or the product mixture may be treated under rearranging conditions (described below) to produce pure [1,5-c]-isomer.

The above product, 7-(3-fluorophenyl)-3-methyl-1,2,4-triazolo[4,3-c]-pyrimidine, may be rearranged to its [1,5-c]-isomer by heating for several hours in formic acid or by heating in refluxing methanol for 6–8 hours or more; 7-(3-fluorophenyl)-2-methyl-1,2,4-triazolo[1,5-c]-pyrimidine is thereby obtained.

EXAMPLES 40 TO 54

The above procedures described in Example 39, both for cyclization and rearrangement, are used to prepare the compounds listed in Table VI ([4,3-c]-isomers) and Table VII ([1,5-c]-isomers.

TABLE VI

7-Aryl-1,2,4-triazolo[4,3-c]pyrimidines

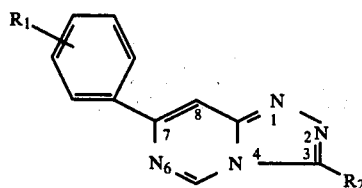

| Example | Compound | Procedure Used | R₁ | R₂ | M.P. °C. |
|---|---|---|---|---|---|
| 40 | 3-Methyl-7-phenyl-1,2,4-triazolo[4,3-c]pyrimidine | triethyl orthoacetate reflux 5 hours | H | CH₃ | 304–306 |
| 41 | 7-(4-Fluorophenyl)-3-methyl-1,2,4-triazolo[4,3-c]-pyrimidine | triethyl orthoacetate reflux 2.5 hours | 4-F | CH₃ | 300–303 |
| 42 | 7-(3-Fluorophenyl)-1,2,4-triazolo[4,3-c]pyrimidine | triethyl orthoformate reflux 5 hours | 3-F | H | 229–233 |
| 43 | 3-Methyl-7-[3-(trifluoromethyl)-phenyl]-1,2,4-triazolo-[4,3-c]-pyrimidine | triethyl orthoacetate 80° C. 2 hours[a] | 3-CF₃ | CH₃ | 151–153 |
| 44 | 7-[3-(trifluoromethyl)-phenyl[-1,2,4-triazolo-[4,3-c]-pyrimidine | triethyl orthoformate 80° C. 2½ hours | 3-CF₃ | H | 207–209 |
| 45 | 7-(4-Fluorophenyl)1,2,4-triazolo[4,3-c]pyrimidine | diethoxymethyl acetate room temperature 2 hours | 4-F | H | 212–215[·b] |
| 46 | 7-(3-Chlorophenyl)-1,2,4-triazolo[4,3-c]pyrimidine | diethoxymethyl acetate room temperature 1 hour | 3-Cl | H | Mixture[c] |
| 47 | 7-(3-Chlorophenyl)-3-methyl- | triethyl | 3-Cl | CH₃ | Mixture[c] |

TABLE VI-continued

7-Aryl-1,2,4-triazolo[4,3-c]pyrimidines

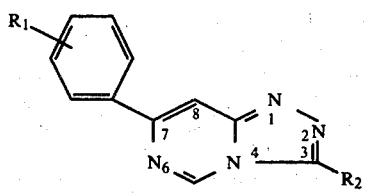

| Example | Compound | Procedure Used | $R_1$ | $R_2$ | M.P. °C. |
|---|---|---|---|---|---|
|  | 1,2,4-triazolo[4,3-c]pyrimidine | orthoacetate 80° C. 5 hours |  |  |  |

Notes:
[a]Reaction for 3 hours gives mixture with [1,5-c]-isomer; treatment with refluxing methanol gives pure [1,5-c]-isomer; See Table VII.
[b]Product contains traces of [1,5-c]-isomer;
[c]Mixture with [1,5-c]-isomer; refluxing methanol completes conversion to [1,5-c]-isomer; See Table VII.

TABLE VII

7-Aryl-1,2,4-triazolo[1,5-c]pyrimidine

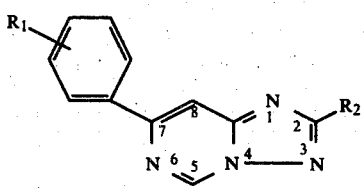

| Example | Compound | Procedure Used | $R_1$ | $R_2$ | M.P. °C. |
|---|---|---|---|---|---|
| 48 | 2-Methyl-7-phenyl-1,2,4-triazolo[1,5-c]pyrimidine | formic acid reflux 3 hours | H | $CH_3$ | 151–153* |
| 49 | 7-(4-Fluorophenyl)-1,2,4-triazolo[1,5-c]pyrimidine | 1 diethoxymethyl acetate 2 methanol,reflux | 4-F | H | 227–229 |
| 50 | 7-(4-Fluorophenyl-2-Methyl-1,2,4-triazolo[1,5-c]-pyrimidine | methanol reflux temperature 20 hours | 4-F | $CH_3$ | 186–187 |
| 51 | 2-Methyl-7-[3-(trifluoromethyl)phenyl]-1,2,4,-triazolo[1,5-c]pyrimidine | methanol reflux temperature 23 hours | 3-$CF_3$ | $CH_3$ | 155–156 |
| 52 | 7-[3-(trifluoromethyl)-phenyl-1,2,4-triazolo-[1,5-c]pyrimidine | 1 diethoxymethyl acetate, 3 hours 2 methanol, reflux 4 hours | 3-$CF_3$ | H | 127–128 |
| 53 | 7-(3-Chlorophenyl)-1,2,4-triazolo[1,5-c]pyrimidine | 1 diethoxymethyl acetate 2 methanol, reflux | 3-Cl | H | 182–184 |
| 54 | 7-(3-Chlorophenyl)-2-methyl-1,2,4-triazolo[1,5-c]pyrimidine | 1 triethyl orthoformate,80°, 5 hours 2 methanol, reflux | 3-Cl | $CH_3$ | 158–159 |

EXAMPLES 55 TO 67

The general procedures described in the preceeding examples are used to prepare the compounds listed in Table VIII, employing the appropriate hydrazine intermediates as listed.

TABLE VIII

Rearrangement of [4,3-c]-isomers to The corresponding [1,5-c]-isomers

| Hydrazine Intermediate | Example | Initial Cyclization Product; [4,3-c]Isomer | Example | Rearranged Product; [1,5-c]-Isomer |
|---|---|---|---|---|
| 1-Formyl-2-[2-(3-trifluoromethyl-phenyl)pyrimidin-4-yl]hydrazine | 24 | 5-[3-(Trifluoromethyl)-phenyl]-1,2,4-triazolo-[4,3-c]-pyrimidine | 55 | 5-[3-(Trifluoromethyl)-phenyl]-1,2,4-triazolo-[1,5-c]pyrimidine |
| 1-Formyl-2-(2-phenyl-pyrimidin-4-yl-hydrazine | 25 | 5-Phenyl-1,2,4-triazolo-[4,3-c]pyrimidine | 56 | 5-Phenyl-1,2,4-triazolo-[1,5-c]-pyrimidine |
| 1-[2-(3-Chlorophenyl)-pyrimidin-4-yl]-2-formyl-hydrazine | 27 | 5-(3-Chlorophenyl)-1,2,4-triazolo[4,3-c]-pyrimidine | 57 | 5-(3-Chlorophenyl)-1,2,4-triazolo[1,5-c]-pyrimidine |

TABLE VIII-continued

Rearrangement of [4,3-c]-isomers to
The corresponding [1,5-c]-isomers

| Hydrazine Intermediate | Example | Initial Cyclization Product; [4,3-c]Isomer | Example | Rearranged Product; [1,5-c]-Isomer |
|---|---|---|---|---|
| 1-[2-(2-Fluorophenyl)-pyrimidin-4-yl]-2-formylhydrazine | 28 | 5-(2-Fluorophenyl)-1,2,4-triazolo[4,3-c]-pyrimidine | 58 | 5-(2-Fluorophenyl)-1,2,4-triazolo[1,5-c]-pyrimidine |
| 1-[2-(4-Fluorophenyl)-pyrimidin-4-yl]-2-formylhydrazine | 30 | 5-(4-Fluorophenyl)-1,2,4-triazolo[4,3-c]-pyrimidine | 59 | 5-(4-Fluorophenyl)-1,2,4-triazolo[1,5-c]-pyrimidine |
| 1-Acetyl-2-[2-(3-chloro-phenyl)-pyrimidin-4-yl]-hydrazine | 60 | 5-(3-Chlorophenyl)-3-methyl-1,2,4-triazolo-[4,3-c]pyrimidine | 61 | 5-(3-Chlorophenyl)-2-methyl-1,2,4-triazolo-[1,5-c]pyrimidine |
| 1-Acetyl-2-[2-(2-fluoro-phenyl)pyrimidin-4-yl]hydrazine | 62 | 5-(2-Fluorophenyl)-3-methyl-1,2,4-triazolo-[4,3-c]pyrimidine | 63 | 5-(2-Fluorophenyl)-2-methyl-1,2,4-triazolo-[1,5-c]pyrimidine |
| 1-Acetyl-2-[2-(4-fluo-rophenyl)pyrimidin-4-yl]hydrazine | 64 | 5-(4-Flourophenyl)-3-methyl-1,2,4-triazolo-[4,3-c]pyrimidine | 65 | 5-(4-Fluorophenyl)-2-methyl-1,2,4-triazolo-[1,5-c]pyrimidine |
| 4-Hydrazino-5-phenyl-pyrimidine | 66 | 8-Phenyl-1,2,4-triazolo[4,3-c]pyrimidine | 67 | 8-Phenyl-1,2,4-triazolo[1,5-c]pyrimidine |

EXAMPLE 68

8-(4-Methoxy-phenyl)-1,2,4-triazolo[1,5-c]-pyrimidine 8-(4-Methoxy-phenyl)-1,2,4-triazolo[4,3-c]pyrimidine, m.p. 167°-169° C., is heated above its melting point at 195°-200° C., for 15 minutes and then cooled to room temperature. The rearranged product of the example is thereby obtained in a substantially pure state, identical with the product of Example 21.

In a similar fashion 5-(3-methoxy-phenyl)-1,2,4-triazolo[4,3-c]pyrimidine, m.p. 183°-185° C., is heated at 195°-200° C., for 15 minutes, and the starting material is recovered unchanged (no rearrangement under these conditions).

We claim:

1. A compound of the formula:

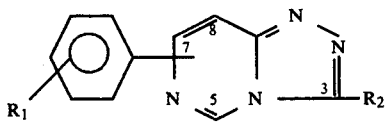

wherein $R_1$ is selected from the group consisting of hydrogen, fluoro, chloro, trifluoromethoxy and alkoxy having up to 3 carbon atoms and $R_2$ is selected from the group consisting of hydrogen and alkyl having up to 3 carbon atoms.

2. The compound in accordance with claim 1; 8-(4-chlorophenyl)-3-methyl-1,2,4-triazolo[4,3-c]pyrimidine.

3. The compound in accordance with claim 1; 8-[3-(trifluoromethyl)phenyl]-1,2,4-triazolo[4,3-c]pyrimidine.

4. The compound in accordance with claim 1; 3-methyl-8-[3-(trifluoromethyl)phenyl]-1,2,4-triazolo[4,3-c]pyrimidine.

5. The compound in accordance with claim 1, 5-phenyl-1,2,4-triazolo[4,3-c]pyrimidine.

6. The compound in accordance with claim 1, 8-(3-fluorophenyl)-1,2,4-triazolo[4,3-c]pyrimidine.

7. The compound in accordance with claim 1, 5-[3-(trifluoromethyl)phenyl]-1,2,4-triazolo[4,3-c]pyrimidine.

8. The compound in accordance with claim 1, 8-(2-chlorophenyl)-3-methyl-1,2,4-triazolo[4,3-c]pyrimidine.

9. The compound in accordance with claim 1, 8-(2-chlorophenyl)-1,2,4-triazolo[4,3-c]pyrimidine.

10. The compound in accordance with claim 1; 5-(3-methoxyphenyl)-1,2,4-triazolo[4,3-c]pyrimidine.

11. The compound in accordance with claim 1; 5-(3-chlorophenyl)-1,2,4-triazolo[4,3-c]pyrimidine.

12. The compound in accordance with claim 1; 5-(2-fluorophenyl)-1,2,4-triazolo[4,3-c]pyrimidine.

13. A compound of the formula:

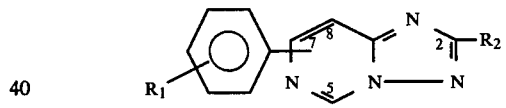

wherein $R_1$ is selected from the group consisting of hydrogen, fluoro, chloro, trifluoromethoxy and alkoxy having up to 3 carbon atoms and $R_2$ is selected from the group consisting of hydrogen and alkyl having up to 3 carbon atoms.

14. The compound in accordance with claim 13; 2-methyl-8-[3-(trifluoromethyl)phenyl]-1,2,4-triazolo[1,5-c]pyrimidine.

15. The compound in accordance with claim 13; 2-methyl-7-phenyl-1,2,4-triazolo[1,5-c]pyrimidine.

16. The compound in accordance with claim 13; 8-(3-fluorophenyl)-2-methyl-1,2,4-triazolo[1,5-c]pyrimidine.

17. The compound in accordance with claim 13; 8-(2-chlorophenyl)-2-methyl-1,2,4-triazolo[1,5 -c]pyrimidine.

18. The compound in accordance with claim 13; 8-(2-chlorophenyl)-1,2,4-triazolo[1,5c-]pyrimidine.

19. The compound in accordance with claim 13; 7-[3-(trifluoromethyl)phenyl]-1,2,4-triazolo[1,5-c]pyrimidine.

* * * * *